(12) United States Patent
Benjamin et al.

(10) Patent No.: US 8,993,587 B2
(45) Date of Patent: Mar. 31, 2015

(54) COMBINATION OF SYROSINGOPINE AND MITOCHONDRIAL INHIBITORS FOR THE TREATMENT OF CANCER AND IMMUNOSUPPRESSION

(75) Inventors: Don Benjamin, Basel (CH); Marco Colombi, Basel (CH); Michael Hall, Basel (CH); Christoph Moroni, Basel (CH)

(73) Assignee: Universitat Basel, Basel (CH)

( * ) Notice: Subject to any disclaimer, the term of this patent is extended or adjusted under 35 U.S.C. 154(b) by 2 days.

(21) Appl. No.: 13/977,811

(22) PCT Filed: Jan. 9, 2012

(86) PCT No.: PCT/EP2012/050216
§ 371 (c)(1),
(2), (4) Date: Jul. 1, 2013

(87) PCT Pub. No.: WO2012/095379
PCT Pub. Date: Jul. 19, 2012

(65) Prior Publication Data
US 2013/0281478 A1    Oct. 24, 2013

(30) Foreign Application Priority Data

Jan. 11, 2011 (GB) .................................. 1100404.1
Aug. 31, 2011 (EP) .................................. 11179599

(51) Int. Cl.
*A61K 45/06* (2006.01)
*A61K 31/155* (2006.01)
*A61K 31/35* (2006.01)
*A61K 31/4375* (2006.01)
*A61K 31/4745* (2006.01)
*A61K 31/625* (2006.01)
*A61K 31/7072* (2006.01)
*A61K 31/365* (2006.01)

(52) U.S. Cl.
CPC ............. *A61K 31/4375* (2013.01); *A61K 45/06* (2013.01); *A61K 31/155* (2013.01); *A61K 31/35* (2013.01); *A61K 31/4745* (2013.01); *A61K 31/625* (2013.01); *A61K 31/7072* (2013.01); *A61K 31/365* (2013.01)
USPC ......................................................... 514/280

(58) Field of Classification Search
USPC ......................................................... 514/280
See application file for complete search history.

(56) References Cited

FOREIGN PATENT DOCUMENTS

| | | |
|---|---|---|
| GB | 2 465 796 | 6/2010 |
| WO | 2008/110491 | 9/2008 |
| WO | WO 2008/110491 A2 * | 9/2008 ........... A61K 31/436 |

OTHER PUBLICATIONS

International Search Report issued Feb. 22, 2012 in International (PCT) Application No. PCT/EP2012/050216.
A. Schubert et al., "Cyclophilin D, a Component of the Permeability Transition-Pore, Is an Apoptosis Repressor", Cancer Research, vol. 64, No. 1, pp. 85-93, Jan. 1, 2004.

* cited by examiner

*Primary Examiner* — Jeffrey S Lundgren
*Assistant Examiner* — Zenab Olabowale
(74) *Attorney, Agent, or Firm* — Wenderoth, Lind & Ponack, L.L.P.

(57) ABSTRACT

The invention relates to a combination of syrosingopine and a mitochondrial inhibitor, e.g. metformin or oligomycin, and the use of the combination of syrosingopine and a mitochondrial inhibitor for the treatment of cancer and for achieving immunosuppression. The invention also relates to a fluorescence-based method for predicting syrosingopine sensitivity of a cancer cell.

4 Claims, 12 Drawing Sheets

Fig. 1A  6.5
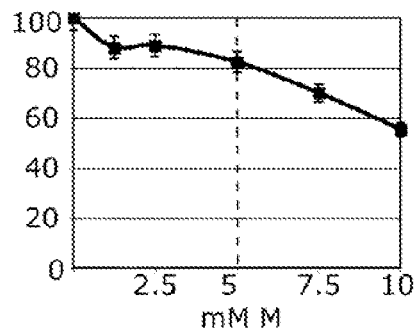
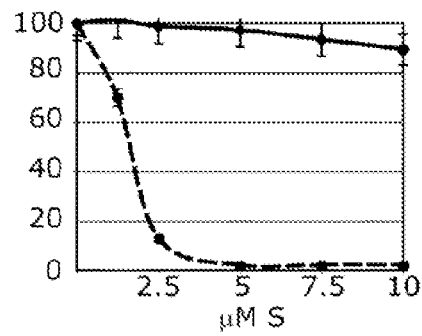
mM M / μM S
Fig. 1B  OPM2
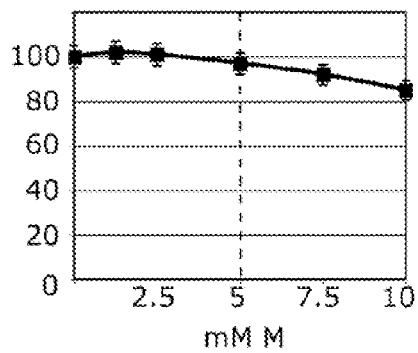
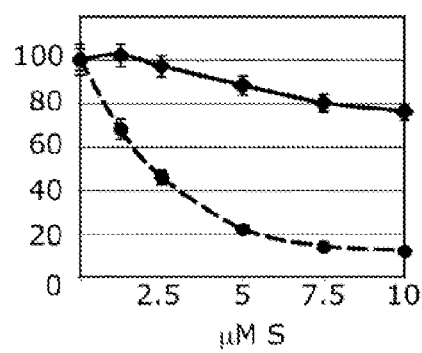
mM M / μM S
Fig. 1C  RPMI-8226
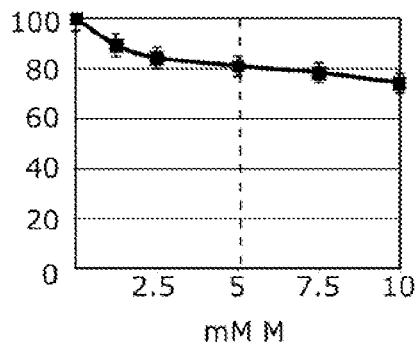
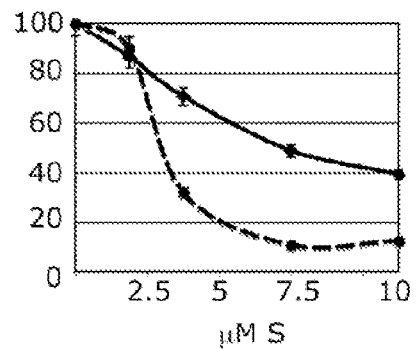
mM M / μM S
Fig. 1D  Jurkat
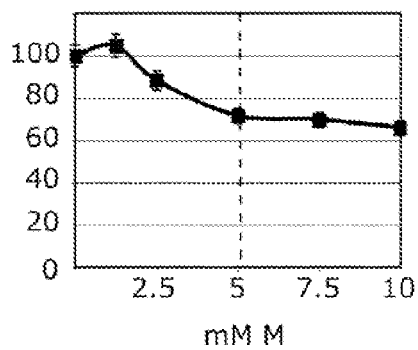
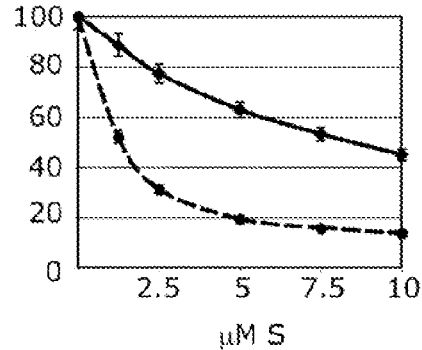
mM M / μM S Fig. 1E  K562
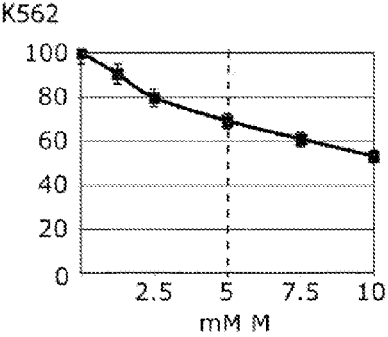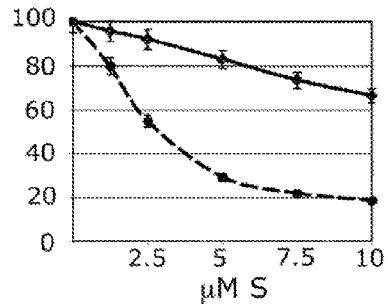
Fig. 1F  HT1080
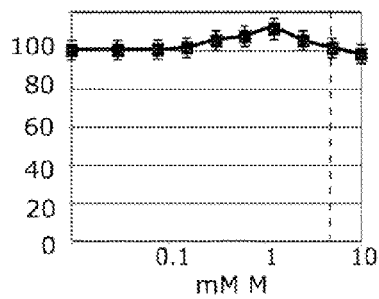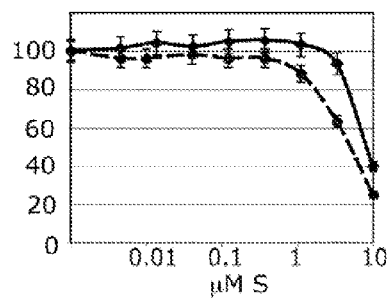
Fig. 1G  Fib3
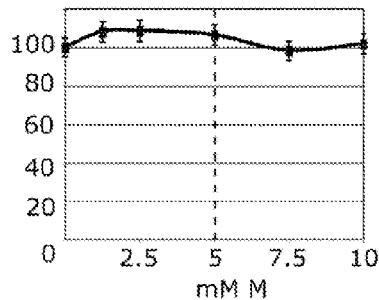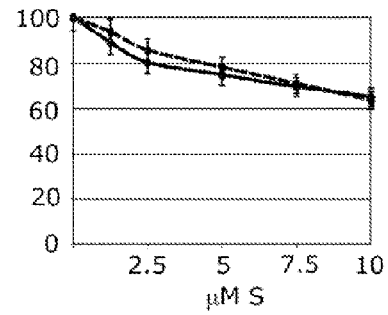
Fig. 1H  Fib4
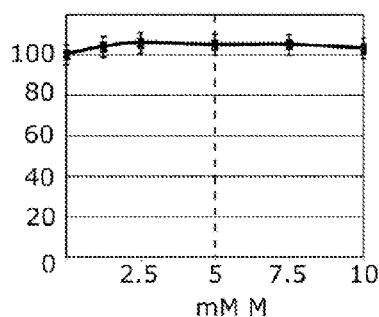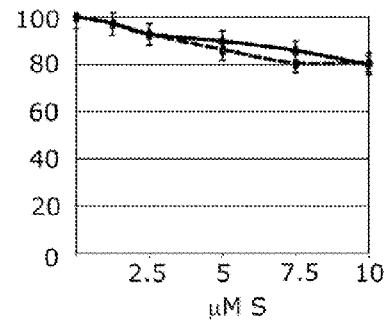

Fig. 2
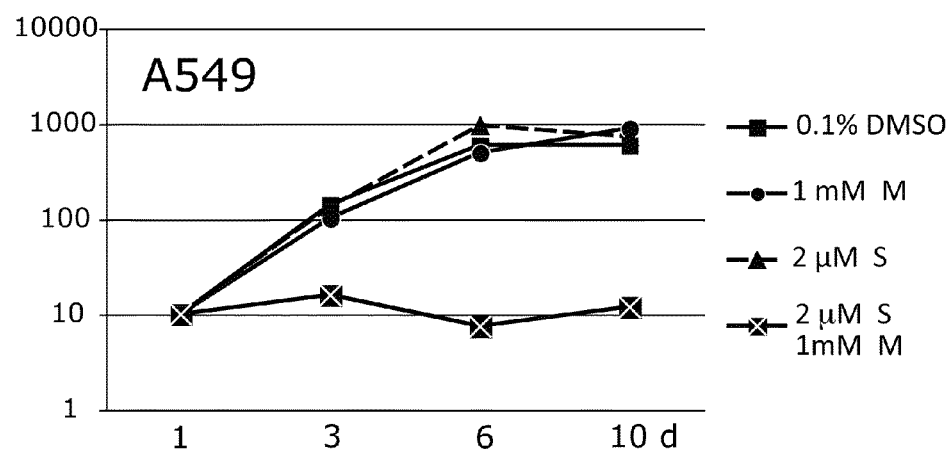
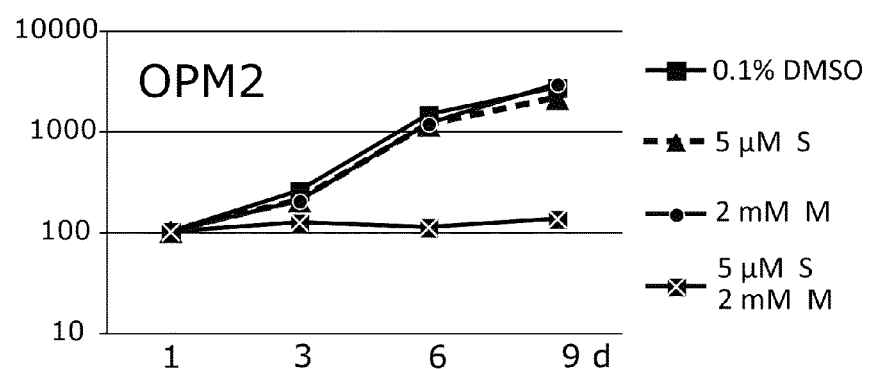

Fig. 3
A) RPMI8226
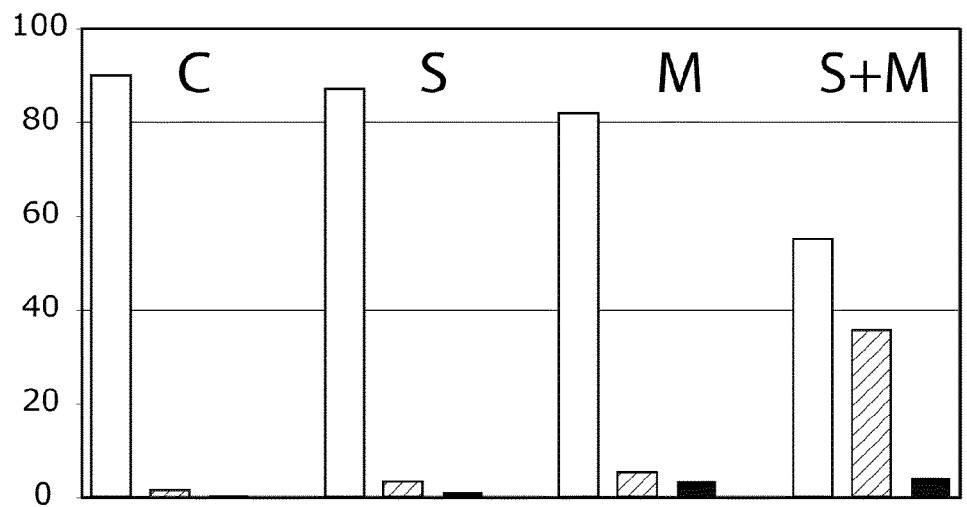
B) OPM2
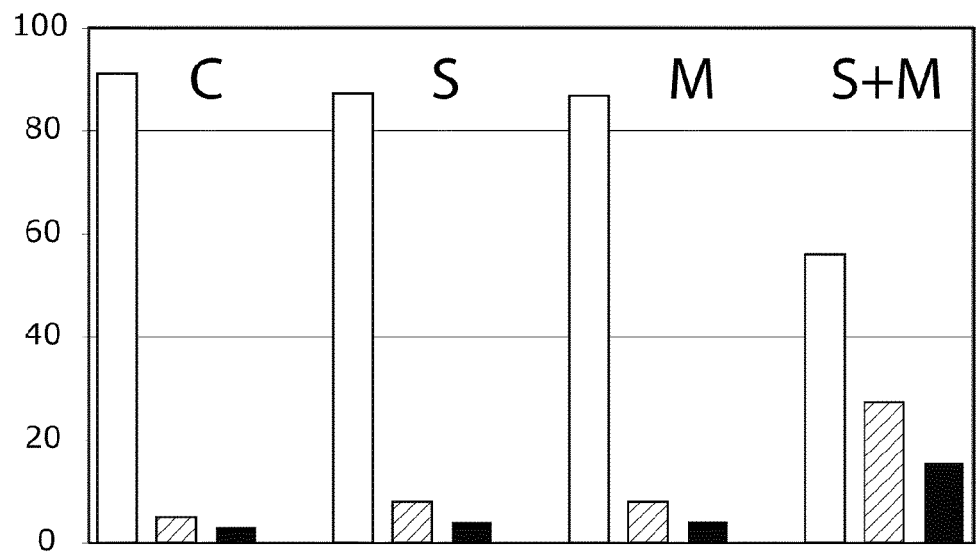

Fig. 4
A) 6.5
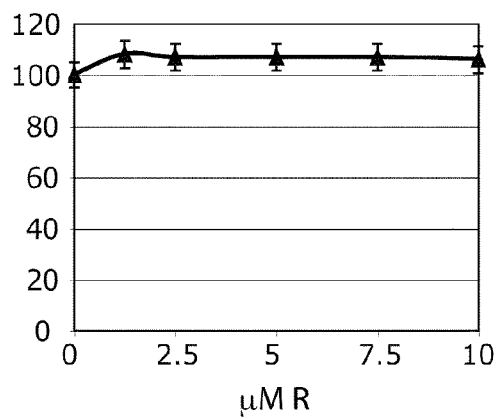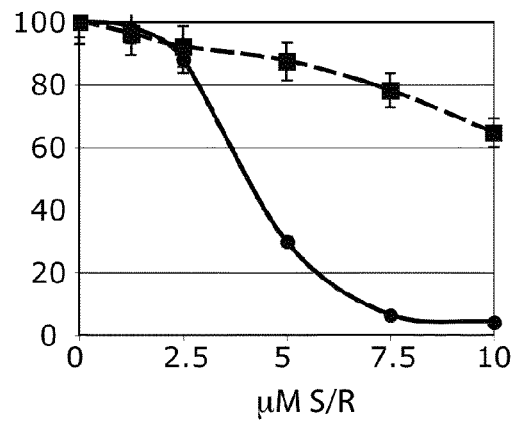
B) OPM2
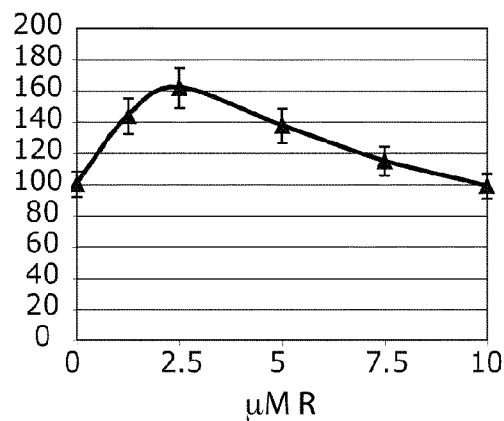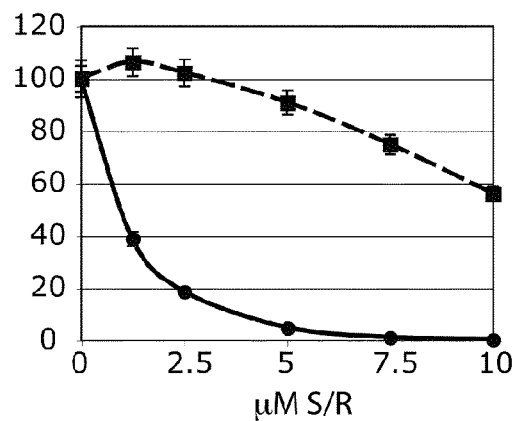

Fig. 5
A)
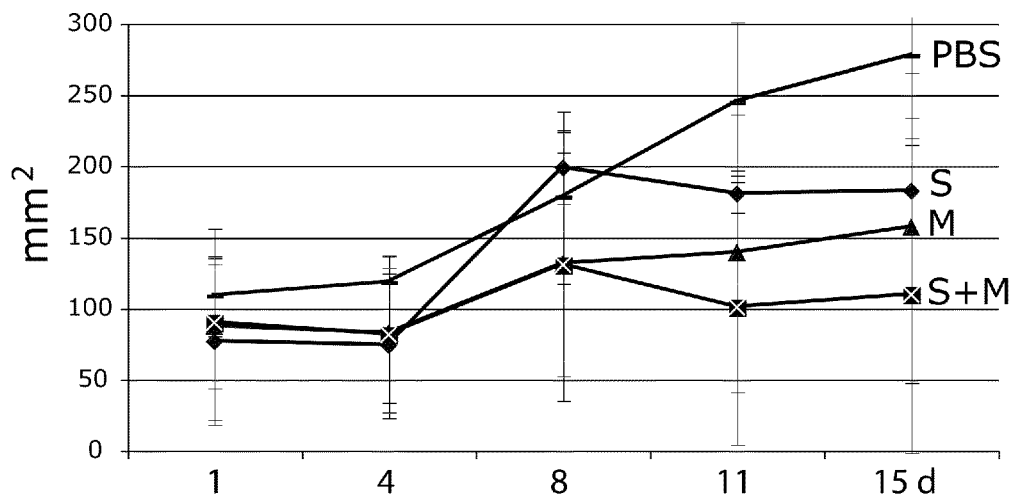
B)
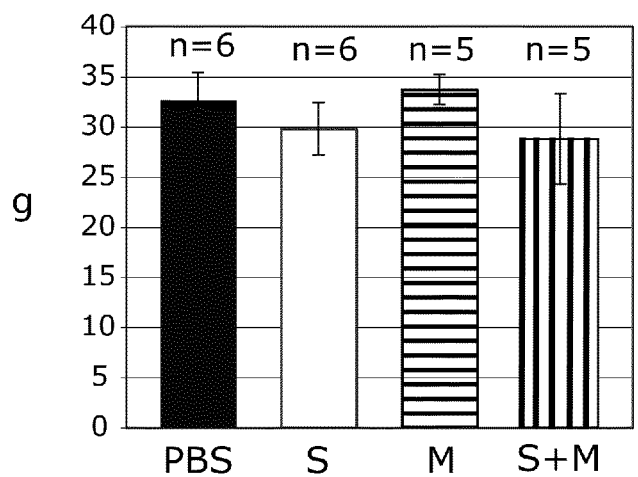

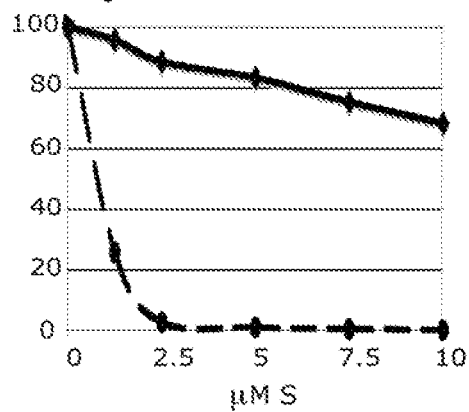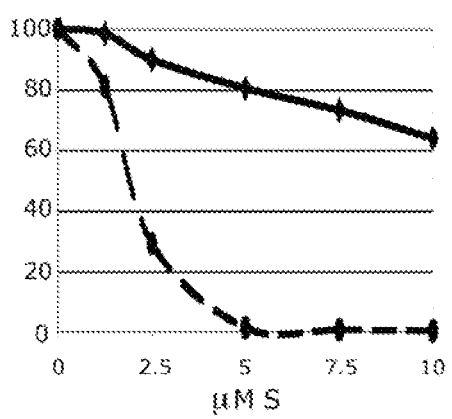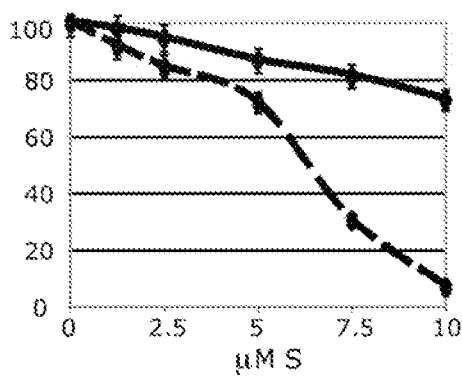

Fig. 10
A) 6.5
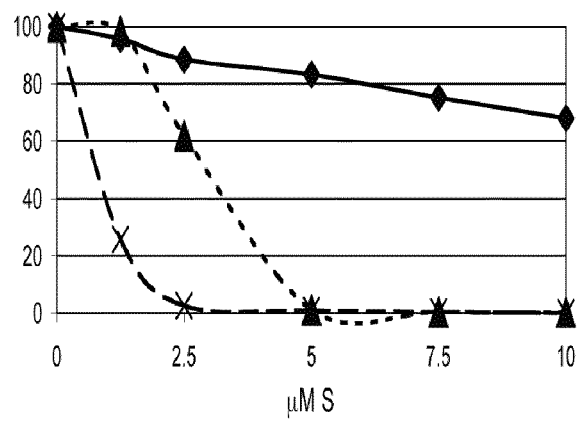
B) HL60
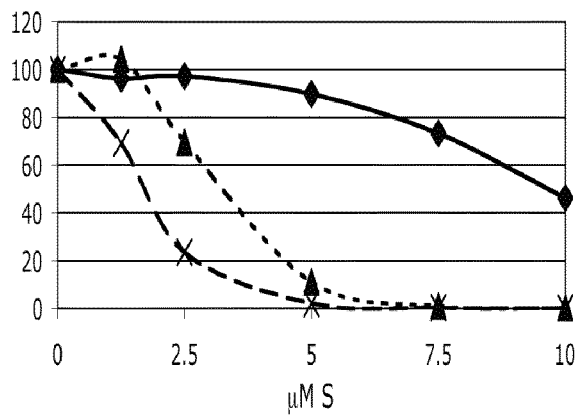
C) OPM2
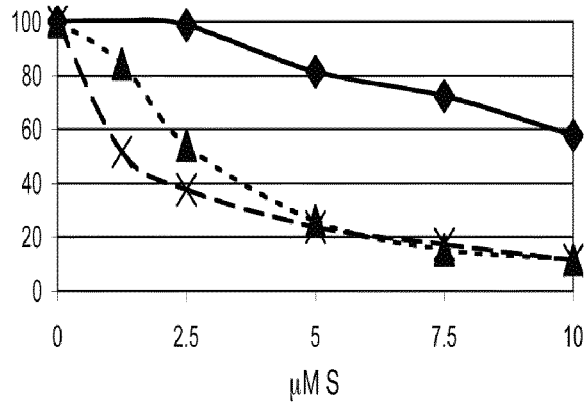

COMBINATION OF SYROSINGOPINE AND MITOCHONDRIAL INHIBITORS FOR THE TREATMENT OF CANCER AND IMMUNOSUPPRESSION

FIELD OF THE INVENTION

The invention relates to a combination of syrosingopine and a mitochondrial inhibitor, e.g. metformin or oligomycin, and the use of the combination of syrosingopine and a mitochondrial inhibitor for the treatment of cancer and for achieving clinical immunosuppression.

BACKGROUND ART

Anti-cancer therapy utilizes a combination of therapeutic interventions such as surgery, radiation therapy and chemotherapy. Surgery and radiation therapy are generally confined locally to the main site of tumor growth, while chemotherapy is applied to prevent tumor re-growth or against distant tumor foci. Chemotherapeutic agents are also used to reduce tumor growth to manage disease progression when radiotherapy or surgery is not an option.

Immunosuppressive agents are clinically used to suppress a pathological immune reaction which targets the own body (autoimmunity) or overshooting immune reactions as seen in allergy. They are also used to treat transplant rejection caused by the immune system. Basic to immune responses is activation and proliferation of T cells following antigenic stimulation, which act in turn as helper cells for B cells, regulatory cells or effector cells. Immunosuppressive agents such as rapamycin or cyclosporine A act by inhibiting early T cell activation/proliferation. As both cancer and immune responses involve cell proliferation, some agents, for example rapamycin or its analogs, were initially used for immunosuppression but found later application as anticancer agents (Recher et al., Blood 2005, 105:2527-34).

Chemotherapeutic drugs are most effectively used in combination therapy. The rationale is to apply drugs that work via different mechanisms in order to decrease the probability of developing drug-resistant cancer cells. Combination therapy also allows, for certain drug combinations, an optimal combined dose to minimize side effects. This is crucial as standard chemotherapeutic agents target essential cellular process such as DNA replication, cell division or induce DNA damage and thus have a general cytotoxic effect. Finally, combination treatment of two compounds may uncover unanticipated synergisms and trigger effects not induced by a single compound. In recent years, drugs are also used in a neoadjuvant setting, i.e. prior to surgery, to reduce the tumor mass or to improve long-term survival.

Syrosingopine is a synthetic derivative of reserpine, an anti-hypertensive and anti-psychotic agent (J.A.M.A., Vol. 170, Nr. 17, Aug. 22, 1959, p. 2092). Syrosingopine was introduced clinically in the late 1950s. The reserpines are rarely used today due to the development of better drugs with fewer side-effects. Reserpine acts by inhibition of the vesicular monoamine transporter leading to catecholamine depletion and this mode of action is believed to be shared by all the reserpine derivatives with an anti-hypertensive effect. Although it has been clinically used, syrosingopine is relatively poorly studied compared to reserpine and has never been investigated as an anti-cancer agent.

Mitochondria contain the energy generating system of a cell, whereby electrons from metabolism pass through complexes I-IV of the electron transfer chain (ETC) leading to extrusion of protons from complex I, III and IV and to a reflux of protons through complex V with concomitant formation of chemical energy in the form of adenosine triphosphate (ATP). Oxygen serves as the ultimate electron acceptor and is reduced to $H_2O$. Critical in this process is the inner mitochondrial membrane, as protons extruded from the complexes pass from the matrix through this membrane into the inter-membrane space, generating a positive membrane potential of 150-200 mV. Dyes such as TMRM (tetramethylrhodamine methyl ester) pass this membrane and accumulate in the mitochondrial matrix, whereby the intensity of the fluorescent signal depends on the strength of the membrane potential. A number of well described agents inhibit mitochondrial function and may be regarded as mitochondriotoxic agents. So called uncoupling agents such as FCCP (carbonyl cyanide-p-trifluoromethoxyphenyl-hydrazone) uncouple the flow of protons from ATP synthesis, leading to a collapse of the membrane potential with resulting loss of ATP synthesis. A number of well described mitochondrial inhibitors target the different complexes of the ETC including metformin, rotenone, epiberberine, piericidin A (all inhibitors of complex I), sodium malonate and thenoyltrifluoroacetone (inhibitors of complex II), antimycin A (complex III inhibitor), potassium cyanide and sodium azide (inhibitors of complex IV), and oligomycin (complex V inhibitor). Mitochondria are believed to be ancestrally engulfed bacteria. They contain a DNA genome encoding several components of the ETC, as well as components of the mitochondrial ribosome. Agents targeting the mitochondrial genome such as certain HIV-inhibitors of the class of nucleoside analogs, e.g. stavudine (D4T), are toxic for mitochondria as they ultimately destroy the ETC and the mitochondrial energy generating system.

Metformin is a widely used biguanide drug for type 2 diabetes. It is related to buformin and phenformin, two biguanides not used anymore in diabetes due to toxicity. Metformin is safe and well-tolerated and has been used in long-term management of diabetes for over 50 years and is the most-prescribed anti-diabetic drug worldwide. The main clinical benefit of metformin in the treatment of type 2 diabetes is the suppression of hepatic gluco-neogenesis to reduce hyperglycemia and improved insulin sensitivity; these effects are believed to be exerted by metformin-dependent stimulation of AMP-activated protein kinase (AMPK) activity. Basic to this effect is the fact, that metformin and other biguanides inhibit complex I of the respiratory chain (electron transfer chain) of mitochondria (El-Mir et al., J Biol Chem 2000, 275:223-228) A meta-analysis of diabetic patients receiving metformin versus an unrelated anti-diabetic agent revealed that the metformin receiving cohort had lower incidence of cancer (Evans et al., BMJ 2005, 330:1304-5; Bowker et al., Diabetes Care 2006, 29:254-8). This has stimulated recent research into the use of metformin as an anti-cancer agent or prophylactic with numerous studies and trials in progress, see Gonzalez-Angulo et al., Clin Cancer Res 2010, 16:1695-700.

SUMMARY OF THE INVENTION

The invention relates to a combination of syrosingopine and a mitochondrial inhibitor, e.g. metformin (and related biguanides phenformin and buformin) or oligomycin, and to pharmaceutical compositions comprising syrosingopine and a mitochondrial inhibitor.

The invention also relates to the use of a combination of syrosingopine and a mitochondrial inhibitor, e.g. metformin (and related biguanides phenformin and buformin) or oligomycin, and of pharmaceutical compositions comprising syrosingopine and a mitochondrial inhibitor for the treatment of cancer, in particular for the treatment of carcinoma, leukemia, myeloma, and lymphoma, and for achieving immunosuppression in autoimmunity, transplantation medicine and in other cases where immunosuppression is desirable, such as diseases of the skin, in particular psoriasis, nervous system, in particular multiple sclerosis, and of the haemopoietic system, in particular anemias; to the use of a combination of syrosingopine and a mitochondrial inhibitor, e.g. metformin (and related biguanides phenformin and buformin) or oligomycin, for the preparation of a pharmaceutical composition for the treatment of cancer and achieving immunosuppression, and to methods of treatment of cancer and of achieving immunosuppression using a combination of syrosingopine and a mitochondrial inhibitor, e.g. metformin (and related biguanides phenformin and buformin) or oligomycin, or of pharmaceutical compositions comprising syrosingopine and a mitochondrial inhibitor.

Furthermore the invention relates to a method for the determination whether a cancerous cell is responsive to syrosingopine combination treatment.

BRIEF DESCRIPTION OF THE FIGURES

FIGS. 1A through 1H: Metformin and Syrosingopine Synergize to Kill Tumor Cells In Vitro.

Figure 6:
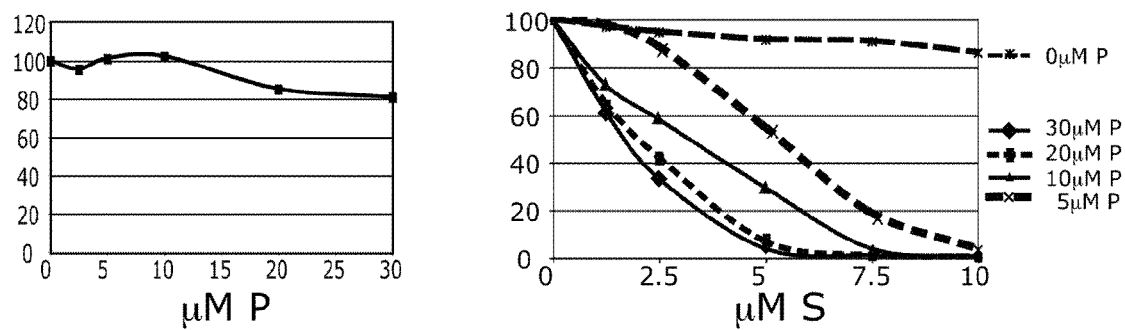

Key: A to H: different cell lines. M=metformin, S=syrosingopine

AlamarBlue conversion cell proliferation assay. Cells were seeded into 96-well microtiter plates and compounds added at the indicated concentration. Seeding cell density ranged from 5,000 to 15,000 cells per well and was determined empirically for each cell type. Plates were incubated for 3 days and proliferation determined by AlamarBlue conversion. Growth was normalized to the untreated controls and shown as percentages (Y-axis). FIGS. 1A through 1E show inhibition curves in a panel of sensitive cells, while FIG. 1F shows the growth curve in non-responding HT1080 fibrosarcoma cells. FIGS. 1G and 1H show results from two non-cancerous normal human fibroblast lines (Fib3 and Fib4). For each cell line the left panel shows a titration of metformin with a dashed vertical line indicating the concentration (5 mM) selected for co-treatment with syrosingopine. Right panel shows a similar growth curve with syrosingopine alone (solid line), and treatment with syrosingopine in the presence of 5 mM metformin (dashed line). All data points were performed in tripliclate.

FIG. 2: Time-Course for Long Term Metformin and Syrosingopine Co-Treatment.

A549 and OPM2 cells were seeded at an initial cell density of 10,000 cells/ml and 100,000 cells/ml, respectively, and compounds (M=metformin, S=syrosingopine) added at the indicated concentrations. For control, cells were incubated with solvent (0.1% DMSO). The wells were sampled at the indicated time points for cell counting (d=days of treatment). Cell density was plotted on the Y-axis (×1000 cells/ml).

FIG. 3: Induction of Apoptosis by Metformin and Syrosingopine Co-Treatment.

OPM2 and RPM18226 cells were seeded at a density of 100,000 cells/5 ml medium with addition of compounds. OPM2: 5 µM syrosingopine (S), 2 mM metformin (M). RPM18226: 2 µM syrosingopine (S), 1 mM metformin (M). No compound=C (control), combination of syrosingopine and metformin=S+M. 500 µl of culture was harvested after 3 days and the cells were washed and stained with propidium iodide/annexin V for FACS (fluorescent activated cell sorter) analysis. Annexin V is an apoptotic marker and was detected using a FITC-coupled antibody on the FL1-channel. Propidium iodide (PI) exclusion staining for vital cells was detected simultaneously on the FL3-channel. For each measurement, the PI and annexin V negative cells represent the viable cell population (white bars). Early apoptotic cells are PI-negative, annexin V-positive (hatched bars) and late apoptotic cells are PI-positive, annexin V-positive (black bars). Bars are plotted on the Y-axis as a percentage of the total cell population.

FIG. 4: The Structurally Related Compound Reserpine does not Synergize with Metformin.

6.5 and OPM2 cells were co-treated with reserpine (R) and metformin (M) over a similar concentration range in parallel with syrosingopine (S). Left panels show the effect on growth proliferation with reserpine alone. Right panels show the growth inhibition of syrosingopine (solid line) or reserpine (dashed line) in the presence of metformin (5 mM). All data points were performed in triplicate. Growth was normalized to the respective untreated controls and expressed as percentages (Y-axis).

FIG. 5: In Vivo Effect of Syrosingopine and Metformin Co-Treatment in a Mouse Syngeneic Tumor Model.

6.5 cells (Colombi et al., Oncogene 2011, 30:1551-65). were injected into the flanks of immunocompatible DBA mice. Drug treatment commenced when tumors reached 100 $mm^2$ in size. Mice were separated into treatment groups and injected intra-peritoneally with PBS (horizontal bars), syrosingopine (S, filled diamonds, 2 mg/kg body weight), metformin (M, filled triangles, 250 mg/kg body weight) and metformin plus syrosingopine (S+M, crossed squares) daily for 15 days. Mice were sacrificed when tumor size became excessive (day 15) and tumors were dissected for measurement. (A) Chart showing tumor area (in $mm^2$) measured over the course of the treatment, d=days. (B) Mean body weight (g) of the mice at the time of sacrifice. Figures (n) above each bar indicate the number of mice per treatment group.

FIG. 6: Syrosingopine Synergizes with the Biguanide Phenformin.

Left panel: 6.5 cells treated with the metformin analogue phenformin (P) for 3 days and growth determined by cell proliferation assay. Right panel: 6.5 cells co-treated with syrosingopine (S) with increasing concentrations of phenformin. Y-axis: % growth relative to untreated controls.

Figure 7:
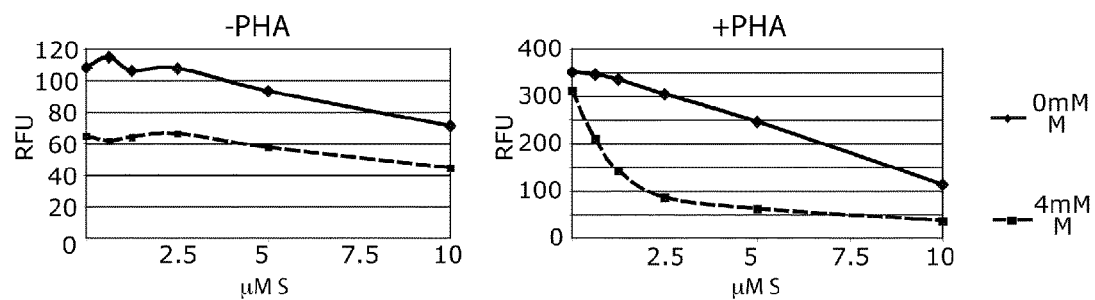

FIG. 7: Co-Treatment of Metformin and Syrosingopine Inhibit Phytohaemagglutinin (PHA)-Stimulated T Cell Proliferation Measured at Day 3.

Human peripheral blood leukocytes were cultured in presence or absence of phytohaemagglutinin. In the presence of phytohaemagglutinin (right panel) the combination of increasing amounts of syrosingopine with 4 mM metformin inhibits sharply T cell proliferation at low concentrations of syrosingopine (dashed line), but not in the absence of metformin (straight line). In the absence of PHA stimulation (left panel), cells survive (as seen microscopically) but do not proliferate at day 3. This survival is only minimally affected by combining syrosingopine with metformin (dashed line).

FIGS. 8A through 8K: Syrosingopine Synergizes with Various Inhibitors of Mitochondrial Function.

Murine 6.5 cells were titrated with syrosingopine (S, solid lines) alone or in the presence of various inhibitors of mitochondrial function (dashed lines): (FIG. 8A) Rotenone 50 nM, (FIG. 8B) Piericidin A 1.25 nM, (FIG. 8C) Epiberberine 0.625 µM, (FIG. 8D) 2-Thenoyltrifluoroacetone (TTFA) 100 µM, (FIG. 8E) Sodium malonate 30 mM, (FIG. 8F) Antimycin A 5 nM, (FIG. 8G) KCN 5 mM, (FIG. 8H) Sodium azide 1.25 mM, (FIG. 8I) Oligomycin 1 nM, (FIG. 8J) Carbonyl cyanide-p-trifluoromethoxyphenyl-hydrazone (FCCP) 10 µM, (FIG. 8K) Stavudine 200 µM. Cells were grown in the presence of the various compounds and growth inhibition measured by a proliferation assay after 3 days of treatment.

Each data point was performed in triplicate and growth was normalized to untreated controls set at 100%.

Figure 9:
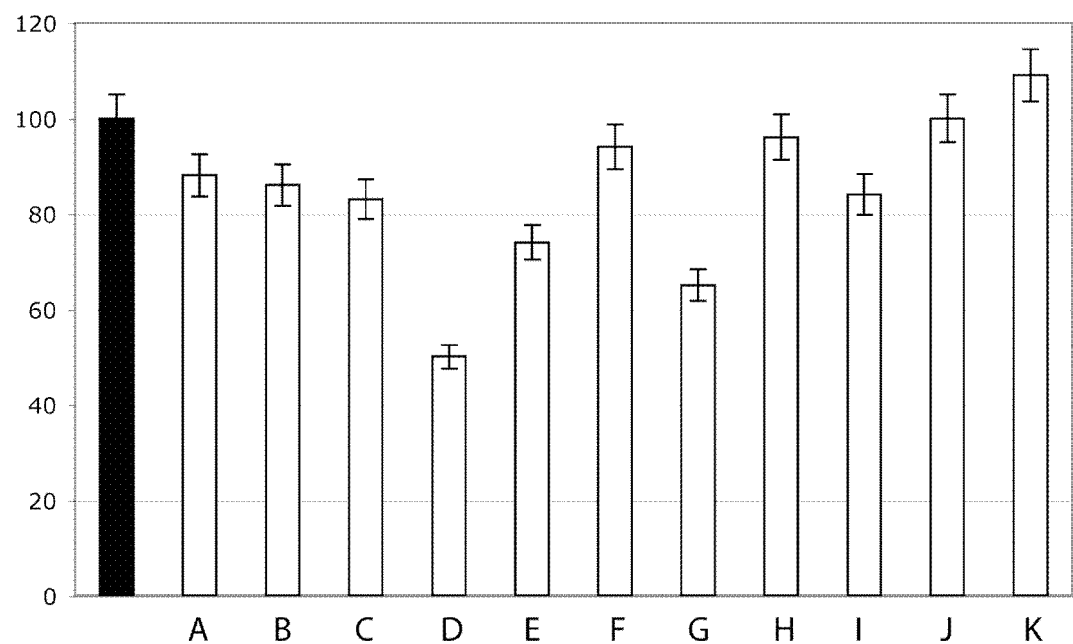

FIG. 9: Inhibitors of Mitochondrial Function Alone do not Kill 6.5 Cells.

Effect of the various mitochondrial targeting agents on growth of 6.5 cells at the concentrations employed for synergistic killing with syrosingopine. Growth is normalized to untreated cells (black bar) set at 100%. Each data point was performed in triplicate and growth was measured after 3 days with a proliferation assay. (A) Rotenone, (B) Piericidin A, (C) Epiberberine, (D) 2-Thenoyltrifluoroacetone, (E) Sodium malonate, (F) Antimycin A, (G) KCN, (H) Sodium azide, (I) Oligomycin, (J) Carbonyl cyanide-p-trifluoromethoxy-phenylhydrazone (FCCP), (K) Stavudine.

FIG. 10: Synergistic Killing of Human Cancer Cells by Syrosingopine and Oligomycin at Subnanomolar Concentration.

A cell growth proliferation assay (3 days) was performed as described in FIG. 1 for (A) mouse cell line 6.5, (B) human promyelocytic leukemia cell line HL60, and (C) human multiple myeloma cell line OPM2. Syrosingopine (S) was titrated in the absence of oligomycin (solid line), in the presence of 500 µM oligomycin (dotted line) and 1 nM oligomycin (dashed line).

Figure 11:
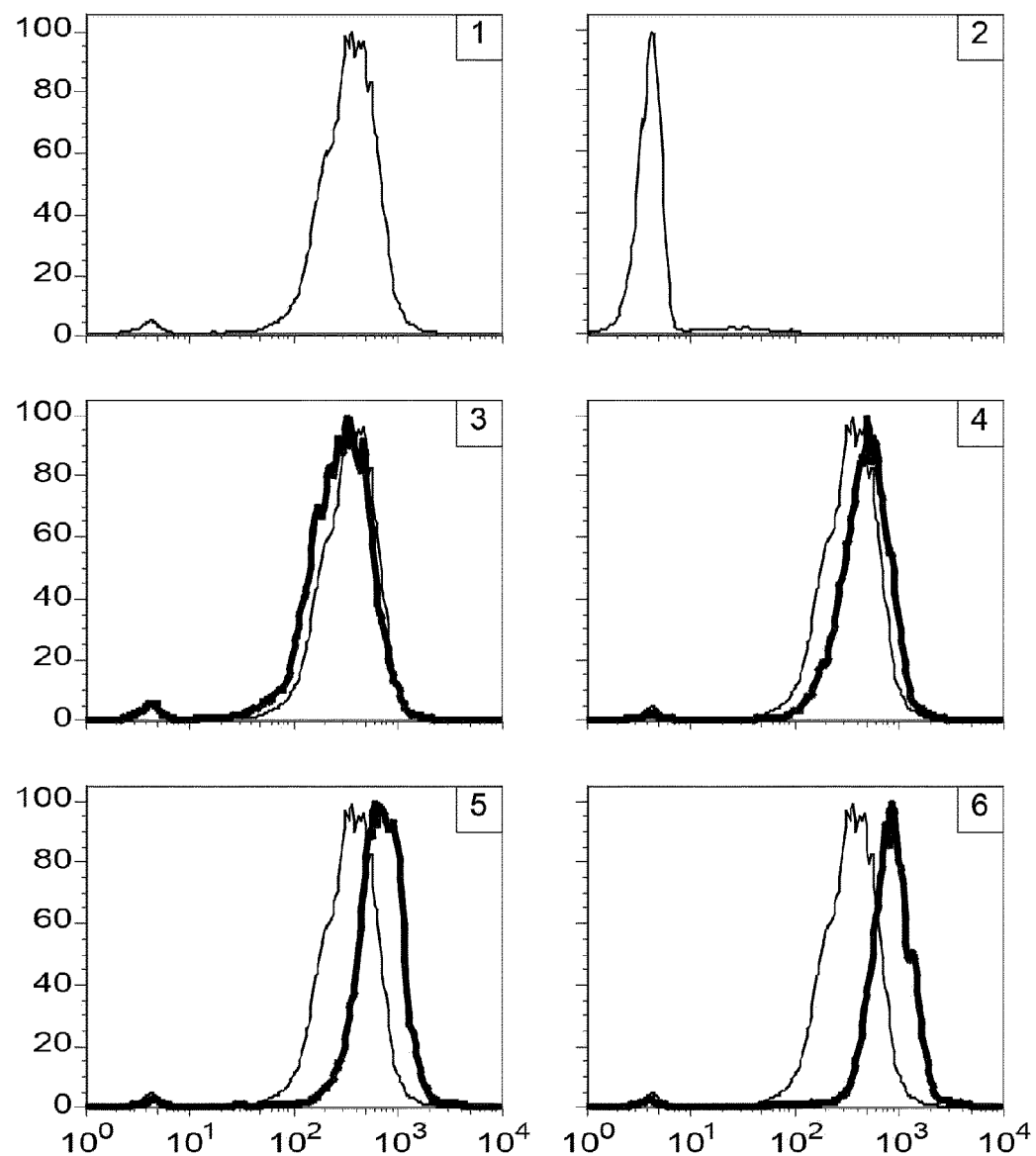

FIG. 11: Syrosingopine Treatment Increases the Mitochondrial Membrane Potential in a Dose-Dependent Fashion.

Murine 6.5 cells were treated with TMRM (panels 1-6), and in addition pre-incubated with FCCP (panel 2), syrosingopine at 0.1 µM (panel 3), 0.5 µM (panel 4), 2 µM (panel 5) or at 5 µM (panel 6) and fluorescence intensity was measured. Thin lines: fluorescence intensity of control cells or FCCP-treated cells (panel 2). Heavy lines indicate cells pre-incubated additionally with syrosingopine (panels 3-6). X-axis indicates fluorescence intensity, Y-axis indicates relative cell numbers. Left shift of the fluorescence peak after FCCP treatment (panel 2) indicates reduction or loss of membrane potential, right shift (panels 4-6) indicates increase of membrane potential upon syrosingopine treatment (compare heavy and thin lines).

DETAILED DESCRIPTION OF THE INVENTION

The invention relates to a combination of syrosingopine and a mitochondrial inhibitor, e.g. metformin or oligomycin, and to pharmaceutical compositions comprising syrosingopine and a mitochondrial inhibitor.

The invention relates furthermore to the use of a combination of syrosingopine and a mitochondrial inhibitor, and of pharmaceutical compositions comprising syrosingopine and a mitochondrial inhibitor for the treatment of cancer, in particular for the treatment of carcinoma, leukemia, myeloma, and lymphoma, and for the treatment of immunological disorders such as autoimmunity.

"Mitochondrial inhibitors" as understood in the present invention comprise compounds which reduce mitochondrial activity and demonstrate varying degrees of mitochondriotoxic properties. Mitochondrial inhibitors comprise so-called uncoupling agents, which uncouple the flow of protons from ATP synthesis in mitochondria, and inhibitors that target different complexes of the electron transfer chain (ETC) in mitochondria, e.g. complex I, complex II, complex III, complex IV, and complex V of the electron transfer chain. Further compounds considered to be mitochondrial inhibitors according to the invention are mitochondriotoxic compounds targeting the mitochondrial genome.

Many widely prescribed drugs exert side effects which are due to mitochondriotoxicity. These mitochondriotoxic drugs are also considered mitochondrial inhibitors according to the invention. Such mitochondriotoxic or mitochondrial inhibitory drugs synergize with syrosingopine and represent anticancer agents when combined with syrosingopine. Mitochondriotoxic drugs have been used for treatment of very different clinical conditions (Cohen et al., Dev Disabil Res Rev 2010, 16:189-199).

Mitochondrial inhibitors according to the invention comprise:

drugs used in liver or gallbladder disease with mitochondrial side effects, such as tetracycline, ibuprofen, amiodarone, pirprofen, tamoxifen, valproate, chloroquine, quinidine, chlorpromazine, ketoconazole, cyclosporine A, rifampicine, and glyburine;

inhibitors of electron transport chain complex I, such as amytal, capsaicin, haloperidol, risperidone, metformin, buformin, phenformin, bupivacaine, lidocaine, halothane, dantrolene, phenyloin, clofibrate, and fenofibrate;

inhibitors of electron transport chain complex II, such as cyclophosphamide and ketoconazole;

inhibitors of electron transport chain complex III, such as antimycin A, acetaminophen, isoflurane, and sevoflurane;

inhibitors of electron transport chain complex IV, such as cephaloridine, cefazolin, and cefalotin;

inhibitors of mitochondrial DNA synthesis, such as AZT (itovudidine), d4T (stavudine), ddI (didanosine), and ddC (zalcitabine);

uncouplers of oxidative phosphorylation, such as pentamidine, indomethacin, fluoxetine, propofol, aspirin, bubivacaine, tolcapone, and dinitrophenol;

agents which reduce molecular oxygen to superoxide via a redox mechanism, such as doxorubicin, isoniazid, gentamycin, and fluoroquinolone; and inhibitors of mitochondrial gene transcription, such as interferon-alpha and interferon-gamma.

Metformin is 3-(diaminomethylidene)-1,1-dimethylguanidine hydrochloride of formula (1)

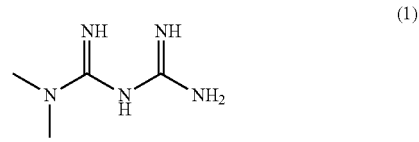

(1)

Other biguanides considered are, for example, phenformin or buformin, preferably phenformin.

Phenformin is 1-(diaminomethylidene)-2-(2-phenylethyl)guanidine of formula (2)

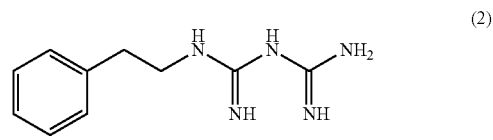 [SMILES: N=C(N)NC(=N)NCCc1ccccc1]

(2)

Syrosingopine is a derivative of reserpine of formula (3),

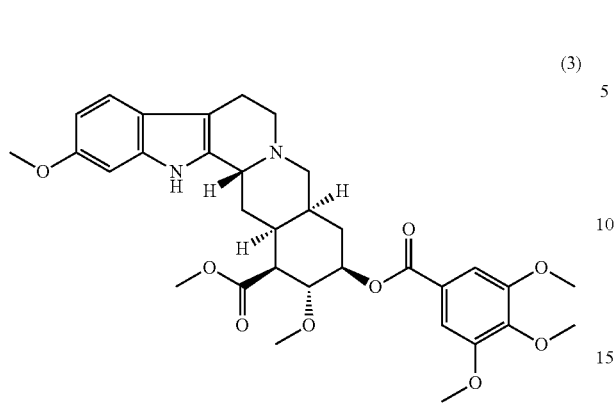

(3)

wherein the 4-methoxy group of the 3,4,5-trimethoxybenzoate part of reserpine is replaced by a 4-ethoxycarbonyloxy group, as shown in formula (4).

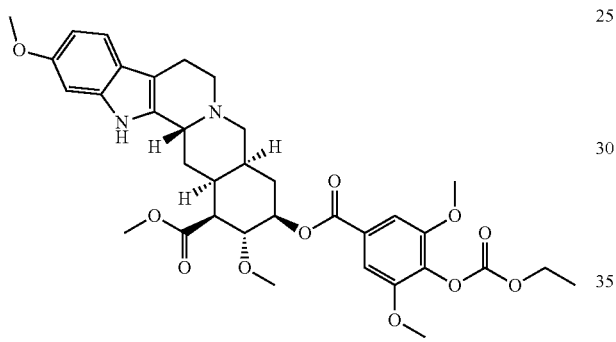

(4)

Further mitochondrial inhibitors shown to synergize with syrosingopine are:

(5A) Rotenone (inhibitor of mitochondrial electron transport chain complex I):

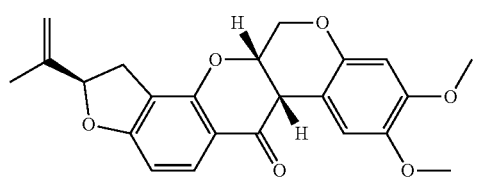

(5A)

(5B) Piericidin A (complex I inhibitor):

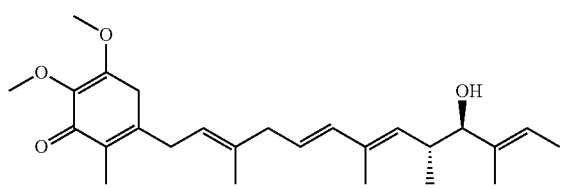

(5B)

5C) Epiberberine (complex I inhibitor):

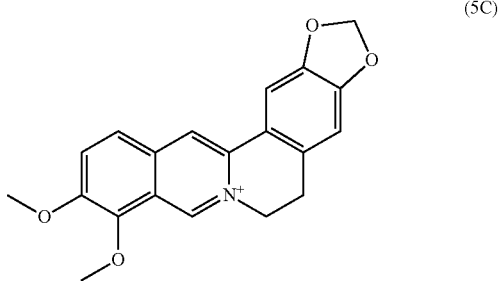 [SMILES: COc1ccc2cc3[n+](cc2c1OC)CCc1cc2c(cc1-3)OCO2]

(5C)

(5D) 2-Thenoyltrifluoroacetone (complex II inhibitor):

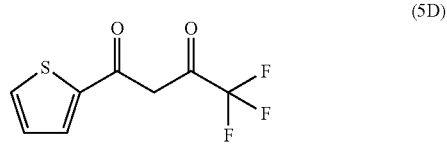 [SMILES: O=C(CC(=O)C(F)(F)F)c1cccs1]

(5D)

(5E) Sodium malonate (complex II inhibitor): $CH_2(COONa)_2$ (5F) Antimycin A (complex III inhibitor):

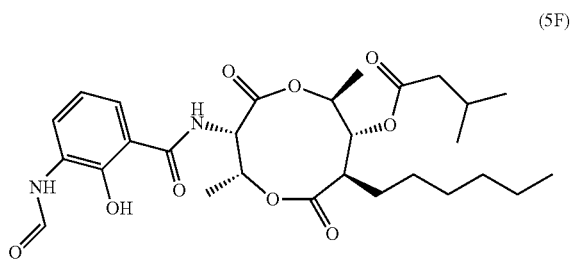 [SMILES: CCCCCC[C@H]1C(=O)O[C@H](C)[C@H](NC(=O)c2cccc(NC=O)c2O)C(=O)O[C@@H](C)[C@@H]1OC(=O)CC(C)C]

(5F)

(5G) Potassium cyanide (complex IV inhibitor): KCN
(5H) Sodium azide (complex IV inhibitor): $NaN_3$
(5I) Oligomycin (complex V inhibitor):

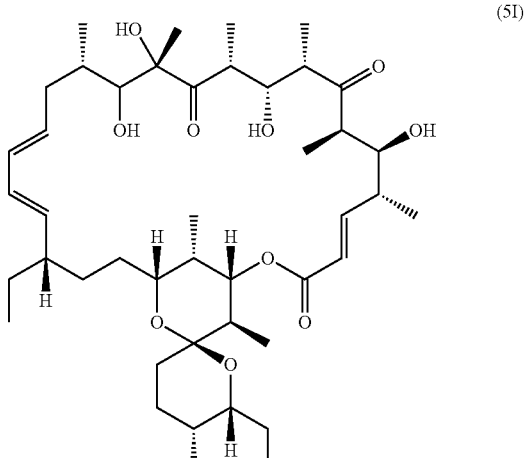

(5I)

(5J) Carbonyl cyanide-p-trifluoromethoxyphenylhydrazone (FCCP) (mitochondrial membrane uncoupling agent):

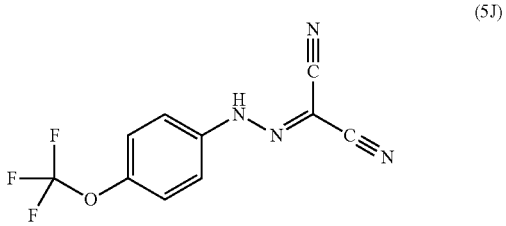 [SMILES: N#CC(C#N)=NNc1ccc(OC(F)(F)F)cc1]

(5J)

and (5K) Stavudine (mitochondrial genotoxic agent):

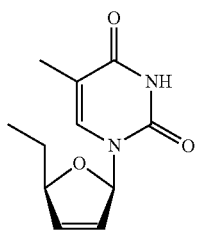

(5K)

In view of the close relationship between basic compounds and their acid addition salts, metformin, phenformin and other mitochondrial inhibitors having a basic nitrogen atom mean the free base or any acid addition salt thereof. Sodium malonate, potassium cyanide and sodium azide are equivalent to other alkali salts, e.g. potassium malonate, sodium cyanide, potassium azide, or also ammonium salts thereof. The kationic compound epiberberine (5C) may carry any pharmaceutically acceptable anion, e.g. chloride, hydrogensulfate, methanesulfonate or dihydrogenphosphate.

Likewise, syrosingopine means the free base or any acid addition salt thereof. Salts are especially the pharmaceutically acceptable salts of syrosingopine.

Such salts are formed, for example, as acid addition salts, preferably with organic or inorganic acids. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantane carboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methyl-benzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

Pharmaceutical compositions according to the invention are, for example, compositions for enteral administration, such as nasal, buccal, rectal or, especially, oral administration, and for parenteral administration, such as intravenous, intramuscular or subcutaneous administration. The compositions comprise syrosingopine and a mitochondrial inhibitor, e.g. metformin or oligomycin, alone or, preferably, together with a pharmaceutically acceptable carrier. The dosage of the combination of syrosingopine and the mitochondrial inhibitor depends upon the disease to be treated and upon the species, its age, weight, and individual condition, the individual pharmacokinetic data, and the mode of administration.

The pharmaceutical compositions comprise from approximately 1% to approximately 95% of the combination of syrosingopine and a mitochondrial inhibitor, e.g. metformin or oligomycin, single-dose administration forms comprising in the preferred embodiment from approximately 20% to approximately 90% combination of syrosingopine and a mitochondrial inhibitor, and forms that are not of single-dose type comprising in the preferred embodiment from approximately 5% to approximately 20% combination of syrosingopine and mitochondrial inhibitor. Unit dose forms are, for example, coated and uncoated tablets, ampoules, vials, suppositories, or capsules. Further dosage forms are, for example, ointments, creams, pastes, foams, tinctures, drops, sprays, and dispersions. Examples are capsules containing from about 0.05 g to about 1.0 g combination of syrosingopine and mitochondrial inhibitor.

The pharmaceutical compositions of the present invention are prepared in a manner known per se, for example by means of conventional mixing, granulating, coating, dissolving or lyophilizing processes.

Preference is given to the use of solutions of the combination of syrosingopine and a mitochondrial inhibitor, e.g. metformin or oligomycin, and also suspensions or dispersions, especially isotonic aqueous solutions, dispersions or suspensions which, for example in the case of lyophilized compositions comprising the combination of syrosingopine and a mitochondrial inhibitor, alone or together with a carrier, for example mannitol, can be made up before use. The pharmaceutical compositions may be sterilized and/or may comprise excipients, for example preservatives, stabilizers, wetting agents and/or emulsifiers, solubilizers, salts for regulating osmotic pressure and/or buffers and are prepared in a manner known per se, for example by means of conventional dissolving and lyophilizing processes. The said solutions or suspensions may comprise viscosity-increasing agents, typically sodium carboxymethylcellulose, carboxymethylcellulose, dextran, polyvinylpyrrolidone, or gelatins, or also solubilizers, e.g. Tween 80® (polyoxyethylene(20)sorbitan monooleate).

Suspensions in oil comprise as the oil component the vegetable, synthetic, or semi-synthetic oils customary for injection purposes. In respect of such, special mention may be made of liquid fatty acid esters that contain as the acid component a long-chained fatty acid having from 8 to 22, especially from 12 to 22, carbon atoms. The alcohol component of these fatty acid esters has a maximum of 6 carbon atoms and is a monovalent or polyvalent, for example a mono-, di- or trivalent, alcohol, especially glycol and glycerol. As mixtures of fatty acid esters, vegetable oils such as cottonseed oil, almond oil, olive oil, castor oil, sesame oil, soybean oil and groundnut oil are especially useful.

The manufacture of injectable preparations is usually carried out under sterile conditions, as is the filling, for example, into ampoules or vials, and the sealing of the containers.

Suitable carriers for preferred solid oral dosage forms are especially fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, also carboxymethyl starch, crosslinked polyvinylpyrrolidone, alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Tablet cores can be provided with suitable, optionally enteric, coatings through the use of, inter alia, concentrated sugar solutions which may comprise gum arabic, talc, polyvinyl-pyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropyl-methylcellulose phthalate. Dyes or pigments may be added to the tablets or tablet coatings, for example for identification purposes or to indicate different doses of the combination of syrosingopine and mitochondrial inhibitor.

Pharmaceutical compositions for oral administration also include hard capsules consisting of gelatin, and also soft, sealed capsules consisting of gelatin and a plasticizer, such as glycerol or sorbitol. The hard capsules may contain the combination of syrosingopine and mitochondrial inhibitor in the form of granules, for example in admixture with fillers, such as corn starch, binders, and/or glidants, such as talc or magnesium stearate, and optionally stabilizers. In soft capsules, the combination of syrosingopine and mitochondrial inhibitor is preferably dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Pharmaceutical compositions suitable for rectal administration are, for example, suppositories that consist of a combination of syrosingopine and a mitochondrial inhibitor, e.g. metformin or oligomycin, and a suppository base. Suitable suppository bases are, for example, natural or synthetic triglycerides, paraffin hydrocarbons, polyethylene glycols or higher alkanols.

For parenteral administration, aqueous solutions of a combination of syrosingopine and a mitochondrial inhibitor, or aqueous injection suspensions that contain viscosity-increasing substances, for example sodium carboxymethylcellulose, sorbitol and/or dextran, and, if desired, stabilizers, are especially suitable. The combination of syrosingopine and mitochondrial inhibitor, optionally together with excipients, can also be in the form of a lyophilizate and can be made into a solution before parenteral administration by the addition of suitable solvents. Solutions such as are used, for example, for parenteral administration can also be employed as infusion solutions.

Preferred preservatives are, for example, antioxidants, such as ascorbic acid, or microbicides, such as sorbic acid or benzoic acid.

On the basis of the studies described in more detail below, the combination of a mitochondrial inhibitor, e.g. metformin of formula (1), phenformin of formula (2), or the further mitochondrial inhibitors of formula (5), in particular oligomycin of formula (5I), and syrosingopine of formula (4), and pharmaceutical compositions comprising a mitochondrial inhibitor and syrosingopine according to the invention show therapeutic efficacy against different types of cancer including carcinomas, sarcomas, gliomas, leukemias, lymphomas, e.g. epithelial neoplasms, squamous cell neoplasms, basal cell neoplasms, transitional cell papillomas and carcinomas, adenomas and adenocarcinomas, adnexal and skin appendage neoplasms, mucoepidermoid neoplasms, cystic neoplasms, mucinous and serous neoplasms, ductal-, lobular and medullary neoplasms, acinar cell neoplasms, complex epithelial neoplasms, specialized gonadal neoplasms, paragangliomas and glomus tumors, naevi and melanomas, soft tissue tumors including sarcomas, fibromatous neoplasms, myxomatous neoplasms, lipomatous neoplasms, myomatous neoplasms, complex mixed and stromal neoplasms, fibroepithelial neoplasms, synovial like neoplasms, mesothelial neoplasms, germ cell neoplasms, trophoblastic neoplasms, mesonephromas, blood vessel tumors, lymphatic vessel tumors, osseous and chondromatous neoplasms, giant cell tumors, miscellaneous bone tumors, gliomas, glioblastomas, oligodendrogliomas, neuroepitheliomatous neoplasms, meningiomas, nerve sheath tumors, granular cell tumors and alveolar soft part sarcomas, Hodgkin's and non-Hodgkin's lymphomas, other lymphoreticular neoplasms, plasma cell tumors, mast cell tumors, immunoproliferative diseases, leukemias including acute and chronic leukemias, miscellaneous myeloproliferative disorders, lymphoproliferative disorders and myelodysplastic syndromes.

On the basis of the studies described in more detail below, the combination of a mitochondrial inhibitor, e.g. metformin of formula (1), phenformin of formula (2), or the further mitochondrial inhibitors of formula (5), in particular oligomycin of formula (5I), and syrosingopine of formula (4), and pharmaceutical compositions comprising a mitochondrial inhibitor and syrosingopine according to the invention show therapeutic efficacy against immunological diseases sensitive to blockade of T cell proliferation including connective tissue diseases such as lupus erythematodes, sclerodermia, polymyositis/dermatomyositis, mixed connective tissue disease, rheumatoid arthritis, Sjögren-syndrome, panarteriitis nodosa, Wegeners granulomatosis; systemic autoimmune diseases such as rheumatoid arthritis, Goodpasture's syndrome, Wegener's granulomatosis, polymyalgia rheumatica, Guillain-Barré syndrome, multiple sclerosis; localized autoimmune diseases such as type 1 diabetes mellitus, Hashimoto's thyroiditis, Graves' disease, celiac disease, Crohn's disease, ulcerative colitis, Addison's disease, primary biliary cirrhosis, autoimmune hepatitis, and giant cell arteritis.

The combination of a mitochondrial inhibitor and syrosingopine, and pharmaceutical compositions comprising syrosingopine and a mitochondrial inhibitor, e.g. metformin or oligomycin, according to the invention may be applied in the form of fixed combinations. Such fixed combination may contain syrosingopine and a mitochondrial inhibitor, e.g. metformin, in a relative amount (weight per weight) of between 1 to 10 and 1 to 1'000, preferably between 1 to 100 and 1 to 200, such as a combination of 1 to 130, whereby the maximum recommended daily dose of metformin based on the experience with diabetes type 2 is 2'550 mg. A fixed combination of syrosingopine and oligomycin may contain syrosingopine and oligomycin in a relative amount (weight per weight) of between 1'000 to 1 and 10'000 to 1. Alternatively, a covalent linkage between syrosingopine and some of the mitochondrial inhibitors, e.g. metformin, may be envisaged. For practical reasons, the salts sodium malonate (5E), potassium cyanide (5G) and sodium azide (5H), although shown to synergize with syrosingopine in cell tests, are not considered combination partners for syrosingopine as anticancer and immunosuppressive agents.

Alternatively, the combination of syrosingopine and a mitochondrial inhibitor, e.g. metformin or oligomycin, may be applied in two different, separate pharmaceutical compositions, optionally being provided together in a kit. The administration of syrosingopine and a mitochondrial inhibitor, e.g. metformin or oligomycin, may also be staggered, or the compounds may be given independently of one another within a reasonable time window.

Pharmaceutical compositions comprising syrosingopine and a mitochondrial inhibitor, e.g. metformin or oligomycin, may be further combined with other chemotherapeutic agents.

Therapeutic agents for possible combination are especially one or more cytostatic or cytotoxic compounds, for example a chemotherapeutic agent or several selected from the group comprising indarubicin, cytarabine, interferon, hydroxyurea, bisulfan, or an inhibitor of polyamine biosynthesis, an inhibitor of the mTOR pathway, an inhibitor of mTOR-complex 1 or mTOR complex 2, an inhibitor of protein kinase, especially of serine/threonine protein kinase, such as protein kinase C, or of tyrosine protein kinase, such as epidermal growth factor receptor tyrosine kinase, a cytokine, a negative growth regulator, such as TGF-β or IFN-β, an aromatase inhibitor, a classical cytostatic, an inhibitor of the interaction of an SH2 domain with a phosphorylated protein, an inhibitor of Bcl-2 and modulators of the Bcl-2 family members such as Bax, Bid, Bad, Bim, Nip3 and BH3-only proteins.

The combination of syrosingopine and mitochondrial inhibitors, e.g. metformin or oligomycin, and pharmaceutical compositions comprising syrosingopine and mitochondrial inhibitors may be administered especially for cancer therapy in combination with radiotherapy, immunotherapy, surgical intervention, or a combination of these. Long-term therapy is equally possible as is adjuvant therapy in the context of other treatment strategies or neo-adjuvant therapy in combination with surgery. Other possible treatments are therapy to maintain the patient's status after tumor regression, or chemopreventive therapy, for example in patients at risk.

The present invention relates furthermore to a method for the treatment of cancer and of immunological disorders such as autoimmunity, which comprises administering a combination of syrosingopine and a mitochondrial inhibitor, e.g. metformin or oligomycin, in a quantity effective against said disease, to a warm-blooded animal requiring such treatment. The combination of syrosingopine and mitochondrial inhibitors, e.g. metformin or oligomycin, can be administered as such or especially in the form of pharmaceutical compositions, prophylactically or therapeutically, preferably in an amount effective against the said diseases, to a warm-blooded animal, for example a human, requiring such treatment. In the case of an individual having a bodyweight of about 70 kg the daily dose administered is from approximately 0.05 g to approximately 3 g, preferably from approximately 0.25 g to approximately 1.5 g, of a combination of the present invention.

The invention relates to the use of a combination of syrosingopine and a mitochondrial inhibitor, e.g. metformin or oligomycin, and of pharmaceutical compositions comprising syrosingopine and a mitochondrial inhibitor for the treatment of cancer, in particular for the treatment of the particular cancers mentioned above. More specifically, the invention relates to the use of a combination of syrosingopine and a mitochondrial inhibitor and of pharmaceutical compositions comprising syrosingopine and a mitochondrial inhibitor for the treatment of carcinomas, sarcomas, leukemias, myelomas, lymphomas, and cancers of the nervous system. Furthermore, the invention relates to the use of a combination of syrosingopine and a mitochondrial inhibitor and of pharmaceutical compositions comprising syrosingopine and a mitochondrial inhibitor for achieving immunosuppression in autoimmunity, transplantation medicine and in other cases where immunosuppression is desirable, in particular in immunological diseases sensitive to blockade of T cell proliferation, systemic autoimmune diseases, and localized autoimmune diseases, as explained above. More specifically, the invention relates to the use of a combination of syrosingopine and a mitochondrial inhibitor, e.g. metformin or oligomycin, and of pharmaceutical compositions comprising syrosingopine and a mitochondrial inhibitor for the treatment of autoimmune diseases, such as autoimmune diseases of the skin, nervous system, connective tissue, muscle, nervous system, blood forming system, bone and inner organs, in particular psoriasis, multiple sclerosis, and anemias.

The preferred relative amount of syrosingopine and mitochondrial inhibitor, e.g. metformin or oligomycin, dose quantity and kind of pharmaceutical composition, which are to be used in each case, depend on the type of cancer or autoimmune disease, the severity and progress of the disease, and the particular condition of the patient to be treated, and has to be determined accordingly by the medical doctor responsible for the treatment.

The invention further relates to the use of a combination of syrosingopine and a mitochondrial inhibitor, e.g. metformin or oligomycin, for the preparation of a pharmaceutical composition for the treatment of cancer or autoimmune disease, as explained above.

Especially, the invention provides a method for treatment of cancer or autoimmune disease, which comprises administering a combination of syrosingopine and a mitochondrial inhibitor, e.g. metformin or oligomycin, or of a pharmaceutical composition comprising syrosingopine and a mitochondrial inhibitor, in a quantity effective against said disease, to a warm-blooded animal requiring such treatment.

Rationale for the Use of a Combination of Syrosingopine and Metformin or Other Biguanides.

A combination screen was performed, where cells were co-treated with the anti-diabetic agent metformin plus over a thousand drugs and drug-like compounds. It was found that metformin and syrosingopine synergize to kill various cancer cells in vitro and in vivo. This effect is only observed when the two drugs are combined, with minimal cytotoxicity for each individual compound.

Mouse mast cell line 6.5 (Colombi et al., Oncogene 2011, 30:1551-65) was used for a preliminary screen. 6.5 cells show many features of oncogenic transformation such as loss of growth-factor (IL3) dependence and signaling pathway addiction. They are addicted to the PI3K-mTOR-Akt pathway as well as to the MAP kinase pathway as shown by inhibitor studies. These cells display exquisite sensitivity to many clinical drugs. A drug co-screen using a commercial drug library (Prestwick Chemical Library) on mouse 6.5 cells in the presence of metformin (2 mM) was performed to identify compounds that would act as a metformin co-drug to kill these cells synergistically.

The best hit identified was syrosingopine. FIG. 1A shows, that metformin alone at 5 mM triggers 20% inhibition of growth (left panel), while syrosingopine alone is virtually non-inhibitory (right panel, straight line). However, when increasing concentrations of syrosingopine are combined with 5 mM metformin (right panel, dashed line), a dramatic inhibition is seen with 2.5 μM syrosingopine. Similar findings were made with a series of human cancer lines, specifically the myeloma line OPM2 (FIG. 1B), the myeloma line RPMI8226 (FIG. 1O), the T cell leukemia line Jurkat (FIG. 1D), the chronic myelogenous leukemia line K562 (FIG. 1E). Notably, in these cell lines the combined activity showed potent activity at a concentration range where each compound used singly had only a marginal effect. In human fibrosarcoma line HT1080 (FIG. 1F) as well as in two normal human fibroblast lines (FIG. 1G, H) no inhibition of growth was observed, when cells were co-treated with both drugs. This is corroboration for a specific response rather than general cytotoxicity, and the lack of activity on normal human fibroblasts indicates that the effect is tumor-specific. Table 1 summarizes data from these and additional lines tested, which together indicate, that the syrosingopine/metformin effect acts upon cancer cells of a wide variety of cancer histotypes, whereby the cell lines used have been widely used in preclinical cancer research and represent accepted and representative models of organ-specific malignancy.

TABLE 1

Panel of human cancer cells tested for sensitivity to metformin and syrosingopine co-treatment.

| Human Cancer Cell | Malignancy | Sensitivity |
| --- | --- | --- |
| OPM1 | Multiple myeloma | YES |
| OPM2 | Multiple myeloma | YES |
| RPMI8226 | Multiple myeloma | YES |
| A549 | Lung cancer (NSCLC) | YES |
| H1299 | Lung cancer (NSCLC) | YES |
| MDA-468 | Breast cancer | YES |
| AN3CA | Endometrial cancer | YES |
| Jurkat | T cell leukemia | YES |
| K562 | Chronic myeloid leukemia | YES |
| HL60 | Promyelocytic leukemia | YES |
| KG1 | Acute myeloblastic leukemia | YES |
| MOLT4 | Acute lymphocytic leukemia | YES |
| HeLa | Cervical cancer | YES |
| JUSO | Melanoma | YES |
| PC3 | Prostate cancer | YES |
| DU145 | Prostate cancer | YES |
| LnCAP | Prostate cancer | YES |
| LN229 | Glioblastoma | YES |
| HT1080 | Fibrosarcoma | NO |
| MDA-231 | Breast cancer | NO |
| U87 | Glioblastoma | NO |
| ME-59 | Melanoma | NO |
| NA-8 | Melanoma | NO |

A time course experiment of the combined treatment was performed on two sensitive human cancer cell lines, OPM2 (multiple myeloma) and A549 (lung cancer). No out-growth was observed after 9-10 days of treatment (FIG. 2). To see whether the inhibition observed involved actual apoptotic cell death, drug-treated cells were analyzed for membrane surface expression of annexin V, a marker of apoptosis, and by propidium iodide (PI) staining, revealing cell death. The number of apoptotic cells was increased with a corresponding decrease in the viable cell population in OPM2 and RPMI8226 human multiple myeloma cells undergoing the combined drug treatment, indicating apoptotic induction as the mechanism of cell killing (FIG. 3). No apoptotic induction was observed when the compounds were used singly.

Syrosingopine of formula (4) is an artificial derivative of reserpine of formula (3), an anti-hypertensive agent, and shares the rauwolfia-specific chemical backbone. Other rauwolfia-related compounds, such as reserpine, reserpinnic acid, rescinnnamine, yohimbinic acid, corynanthine HCl, ajmalicine, yohimbine HCl, and rauwolscine HCl do not show significant interaction with metformin of formula (1) in cancer test cell lines. To confirm the specificity for syrosingopine, reserpine was tested over a range of concentrations in 6.5 and OPM2 cells. No interaction of reserpine with metformin was observed (FIG. 4), suggesting that syrosingopine is acting in a novel fashion compared to other rauwolfia derivatives.

To test if the interaction also holds in an in vivo context, 6.5 cells were injected into immunocompatible DBA mice. Treatment was begun when the tumors reached 100 mm$^2$ in size. Mice were injected intra-peritoneally daily with syrosingopine (2 mg/kg body weight), metformin (250 mg/kg body weight) or both for 15 days and sacrificed for tumor dissection and measurement. As seen in FIG. 5A, the dual treatment successfully arrested tumor growth. There was no significant difference in body weight between the treatment groups (FIG. 5B) or any signs of overt toxicity.

Metformin is a biguanide similar to phenformin (formula 2), an antidiabetic compound which is rarely in clinical use today due to side effects (lactic acidosis). It was tested whether phenformin also synergizes with syrosingopine. As shown in FIG. 6, left panel, phenformin treatment alone leads to no growth inhibition at concentrations up to 10 µM. When phenformin at this concentration, however, is combined with increasing concentrations of syrosingopine (FIG. 6, right panel), a strong synergistic effect is seen. In fact, a dose dependent synergistic effect is observed at all concentrations of phenformin tested.

The triggering of an immune response by antigenic stimulation involves early proliferation of T cells. This T cell stimulation can be mimicked by polyclonal stimulators such as lectins, for example phytohaemagglutinin (PHA). The combination of metformin and syrosingopine also inhibits PHA-stimulated T cell proliferation. Leukocytes isolated from the peripheral blood of normal human blood donors were tested, and proliferation measured on day 3 after incubation with metformin, syrosingopine, or both. As shown in FIG. 7, right panel, PHA-stimulated proliferation is very sensitive to inhibition when syrosingopine is combined with metformin (4 mM) (dashed line), but considerably less so in absence of metformin (solid line). The left panel of FIG. 7 shows peripheral blood leukocytes cultured for 3 days in the absence of PHA, where cells hardly proliferate but survive. This survival is not affected by the presence of increasing concentrations of syrosingopine in presence of 4 mM metformin (dashed line).

Figure 8A:
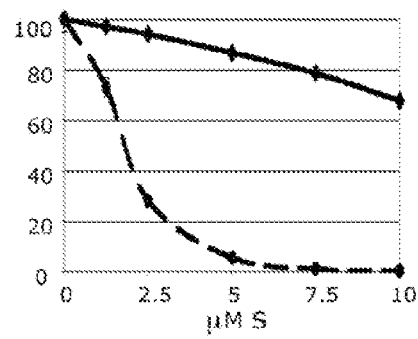
Figure 8B:
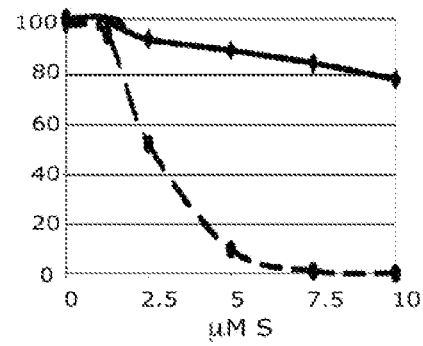
Figure 8C:
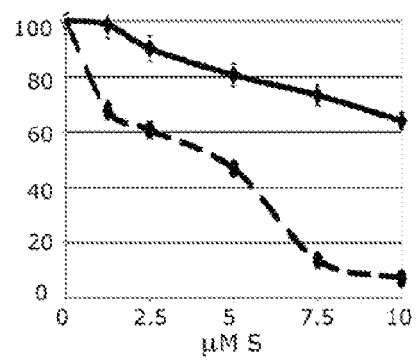
Figure 8D:
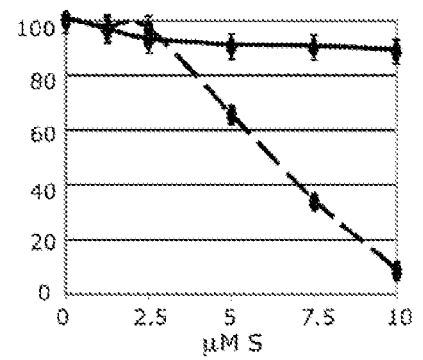
Figure 8E:
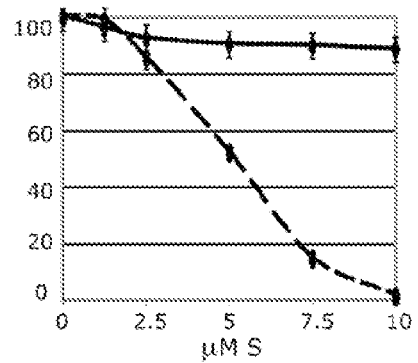
Figure 8F:
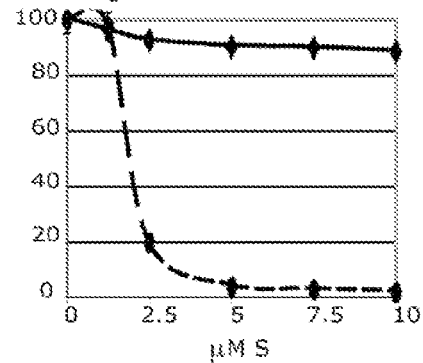
Figure 8G:
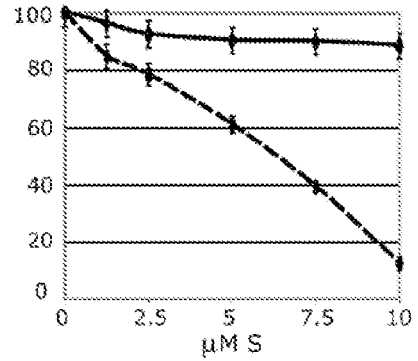
Figure 8H:
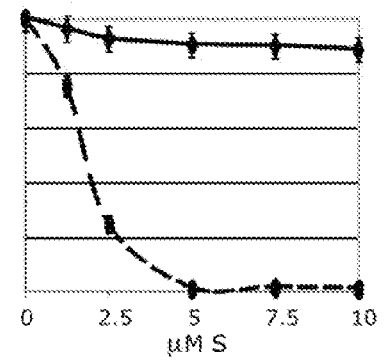

Rationale for the Use of a Combination of Syrosingopine and a Mitochondrial Inhibitor Other than Metformin The fact that metformin blocks complex I of the ETC raised the question whether other inhibitors of the ETC or other mitochondriotoxic agents may similarly co-operate with syrosingopine in cell killing. A series of agents well known to target mitochondria was tested, and concentrations of these agents were used which are not or only minimally toxic by themselves. The agents and the concentrations used are shown in FIGS. 8 and 9. When tested in collaboration with increasing amounts of syrosingopine, synergistic killing with the ETC complex I inhibitors rotenone (FIG. 8A), piericidin A (FIG. 8B), epiberberine (FIG. 8C) was detected. Synergistic killing was likewise detected with the complex II inhibitors TTFA (FIG. 8D) and sodium malonate (FIG. 8E), as well as with the complex III inhibitor antimycin A (FIG. 8F). Two complex IV inhibitors, namely KCN (FIG. 8G) and sodium azide (FIG. 8H) as well as the complex V inhibitor oligomycin (FIG. 8I) also induced synergistic cell killing with syrosingopine. These data establish that syrosingopine induces cell killing when applied together with mitochondrial inhibitors, in this case with ETC inhibitors. FCCP is an agent which uncouples the ETC chain from ATP synthesis. Importantly, this agent also induced synergistic killing with syrosingopine (FIG. 8J). As several components of the ETC are encoded by the mitochondrial genome, one would expect that agents which damage the mitochondrial genome would similarly synergize with syrosingopine. The anti-HIV compound stavudine, a reverse transcriptase inhibitor with well described detrimental side effects on mitochondrial genome replication, was tested. As shown in FIG. 8K, stavudine indeed induced synergistic killing with syrosingopine. Of note, the HIV reverse transcriptase inhibitor 3TC (also known as lamivudine and lacking anti-mitochondrial toxicity) did not synergize with syrosingopine. The results of these experiments lead to the conclusion that ETC inhibitors in general, but also anti-mitochondrial agents which compromise ETC function indirectly, synergize with syrosingopine and are anti-cancer agents and immunosuppressive agents when used at non-toxic concentrations but in combination with syrosingopine.

For practical reasons, the salts sodium malonate, potassium cyanide and sodium azide, although shown to synergize with syrosingopine in cell tests, are not considered combination partners for syrosingopine as anti-cancer and immunosuppressive agents. An interesting combination partner for syrosingopine, however, is for example oligomycin, as even at a concentration below 1 nM this compound kills human cancer lines in combination with syrosingopine (FIG. 10), being without toxic effect in the absence of syrosingopine (FIG. 9).

In Vitro Test Indicating Syrosingopine Sensitivity

In view of the foreseen application of syrosingopine to cancer therapy, it is important to have an in vitro test predicting sensitivity of a cancer cell. Since there are good reasons that the functional target is mitochondrial (as with metformin), the effect of syrosingopine on the membrane potential of the inner mitochondrial membrane was tested. The membrane is more positively charged outside (i.e. in the inter-membrane space) than inside (in the mitochondrial matrix) as mitochondrial respiration involves extrusion of protons from the mitochondrial matrix through the inner membrane into the inter-membrane space. The matrix, being more negatively charged, accumulates positively charged lipophilic molecules such as TMRM (tetramethylrhodamine methyl ester). As TMRM is fluorescent, it functions as a potentiometric dye and lends itself to easy assessment of mitochondrial membrane potential. In FIG. 11 (panels 3-6) it is shown that increasing amounts of syrosingopine lead to an increase of the fluorescent TMRM signal (shift to the right) indicating increased positive membrane polarity. The fluorescence peak shifts from 403 (panel 1) to 955 (panel 9) arbitrary units. Use of FCCP, an uncoupling agent used for control (panel 2), leads to the expected collapse of the membrane potential (as shown by the left-shift of the fluorescence peak down to 42 arbitrary units). While the perturbation of this critical membrane function by syrosingopine is likely to contribute to its synergistic activity with metformin, a known weak mitochondrial inhibitor, the discovery of a mitochondrial effect of syrosingopine allows to perform a straightforward test for syrosingopine-sensitivity of cancer cells.

Based on these results, the invention further relates to a method for the determination whether a cancerous cell is responsive to syrosingopine treatment comprising the steps of (a) preparation of single cell suspension and culturing the cancerous cell in a suitable media, (b) incubating the cancerous cell with syrosingopine, (c) incubating the cancerous cell of step (b) with a positively charged fluorescent dye, (d) measuring the excitation fluorescence intensity, and (e) comparing the measured fluorescence intensity of step (d) with the measured fluorescence intensity of the cancerous cell incubated with the positively charged fluorescent dye alone, and wherein a relative increase of fluorescence intensity of cancerous cells pre-incubated with syrosingopine indicates syrosingopine treatment responsiveness.

For practical purposes the cancerous cell is a cell isolated from a potential patient to be treated with a combination of syrosingopine and a mitochondrial inhibitor. Suitable media for culturing such cancerous cells are well known in the art, and include, for example Iscoves modified Dulbecco medium (IMDM) or RPMI 1640 medium. Prior to testing, a single cell suspension from the ex vivo tumor material has to be prepared. Again, suitable standardized commercial methodologies are at hand, where physical disruption and enzymatic digestion steps are combined (see for example the method by MiltenyiBiotec (http://www.miltenyibiotec.com/downloads/6760/6764/30501/PDF1.pdf) or by Invitrogen (http://www-.invitrogen.com/etc/medialib/en/filelibrary/pdf.Par.18492.File.dat/Dissociation Cells Y14477 Dissociation.pdf)). For testing, it is advisable to preincubate the cancerous cell with different concentrations of syrosingopine, e.g. 0.1 µM and 10 µM, for 2 to 8 h. A suitable positively charged fluorescent dye is TMRM (tetramethylrhodamine methyl ester perchlorate). Other positively charged fluorescent dyes considered are the rhodamines TMRE (tetramethylrhodamine ethyl ester perchlorate), Rhodamine 123 (rhodamine methyl ester chloride), Rhodamine B (tetraethylrhodamine hydrochloride), MitoTracker Red CMXRos® (CAS designation 1H,5H,11H, 15H-xantheno[2,3,4-ij:5,6,7-i'j']diquinolizin-18-ium, 9-[4-(chloromethyl)phenyl]-2,3,6,7,12,13,16,17-octahydro-, chloride), and the carbocyanines JC-1 (5,5',6,6'-tetrachloro-1,1',3,3'-tetraethylbenzimidazolocarbocyanine iodide) and $DiOC_6(3)$ (3,3'-dihexylbenzoxazolocarbocyanine iodide).

Staining with the preferred fluorescent dye TMRM (tetramethylrhodamine methyl ester) is preferably done according to standard methods, such as indicated by the supplier Serotec. Fluorescence is measured at 575 nm after excitation at 488 nm, preferably in a standard commercially available flow cytometer.

If the cancerous cell shows responsiveness to syrosingopine, the corresponding patient will probably be effectively treated by combinations of syrosingopine and a mitochondrial inhibitor. If the cancerous cell is not responsive to syrosingopine in the corresponding fluorescence test with TMRM, chances are low that the patient can be effectively treated with combinations of syrosingopine and a mitochondrial inhibitor.

EXAMPLES

Cell Culture

Mouse mast cell line 6.5 (Colombi et al., Oncogene 2011, 30:1551-65) was cultured in IMDM, 10% FCS, 2 mM L-glutamine, 100 U/ml penicillin, 100 µg/ml streptomycin and 50 µM 2-mercaptoethanol, exogenous IL-3 was added as 1% conditioned medium from X63 murine IL3 secreting cells. Human leukemia cell lines Jurkat, K562, OPM1, OPM2, RPMI8226 were grown in RPM1-1640 medium supplemented with 10% FCS, 2 mM L-glutamine. Recombinant human IL-6 (Biomol) was added at 10 ng/ml to the media for OPM2 and RPM18226. Other human cancer lines MDA-468, MDA-231, A549, H1299, AN3CA, JUSO, HT1080, ME-59, HL60, KG1, MOLT4, HeLa, PC3, DU145, LnCAP. LN229, U87 and NA-8 were grown in Iscove's medium containing 10% FCS, 2 mM L-glutamine and 50 µM 2-mercaptoethanol. All cells were grown at 37° C. in 5% $CO_2$.

Reagents

Metformin and phenformin (Sigma) were prepared as 1M stocks in PBS and kept at 4° C., syrosingopine (Extrasynthese) and reserpine (Sigma) were prepared as 5 mM stock in DMSO and stored at −20° C. Stocks of pieridicin A, epiberberine, TTFA, antimycin A, oligomycin (Sigma) and FCCP were prepared in DMSO; sodium malonate, KCN and NaN$_3$ were dissolved in sterile, distilled water, and rotenone and stavudine stock solutions were made in absolute ethanol.

Mouse Mast Cell Line 6.5

The cell line 6.5 has recently been described (Colombi et al., Oncogene 2011, 30:1551-65). These cells were generated by treating 15V4 mast cells (Nair et al., Oncogene 1992, 7:1963-72) with mutagen ICR191, which led to loss of the Pten tumor suppressor gene. This loss abrogated the IL-3 dependence of the cells and generated growth autonomous cells which formed tumors in syngeneic mice.

Inhibitor Studies of Mouse Mast Cell Line 6.5

Mouse mast cell line 6.5 cells are addicted to the PI3K-mTOR-Akt pathway as well as to the MAP kinase pathway as shown to their sensitive to nanomolar concentrations of the mTOR-inhibitor rapamycin (Colombi et al., Oncogene 2011, 30:1551-65) or the MEK inhibitor U0126.

Cell Proliferation Assay

Cells were seeded at appropriate density (5,000-15,000 cells per well depending on cell type, 150 µl medium per well) in flat-bottomed 96-well plates and compounds added at the desired concentrations. After 3 days, proliferation was assayed by adding 0.1 vol. AlamarBlue (Invitrogen), and fluorescence was read at 535/595 nm excitation/emission after 4-6 hours of color development. Readings were normalized to non-treated control cells and growth expressed as percentage of control growth.

Apoptosis Assay

Apoptosis was determined by Annexin V-FITC (Invitrogen) and propidium iodide counter-staining, and cells were analysed by FACS to distinguish between viable/early apoptotic/late apoptotic cell sub-populations. Cells were seeded at a density of 100,000 cells/5 ml medium with addition of compounds as indicated. 500 µl of culture was harvested after 3 days and the cells were washed and stained with PI/Annexin V before FACs analysis.

Mouse Syngeneic Tumor Model $4 \times 10^5$ 6.5 cells were injected in 150 µl of PBS into the flanks of immuno-compatible DBA mice. Tumor progression was monitored and treatment was started when tumor area reached 100 mm$^2$ in size. Mice were injected intra-peritoneally daily with metformin (250 mg/kg body weight), syrosingopine (2 mg/kg body weight) or combined for 15 days before being sacrificed for tumor tissue measurements.

A Combination of Metformin and Syrosingopine Kills Mouse Mast Cells 6.5

A drug co-screen was performed using a commercial drug library (Prestwick Chemical Library) on mouse 6.5 cells in the presence of metformin (2 mM) to identify compounds that would act as a metformin co-drug to kill these cells synergistically.

Effect of Metformin and Sysrosingopine on Phytohaemagglutinin-Stimulated T Cell Proliferation Normal human buffy coat cells were obtained from a local blood donation center in accordance with the ethical guidelines. 80 ml of blood was diluted with 200 ml of Iscove's medium and overlayed on a Ficoll gradient. The gradient was centrifuged at 1400×g for 5 minutes to separate the leukocyte fraction from erythrocytes. Cells were plated on coated tissue culture dishes for 1 hour to remove adherent cells, and the remaining suspension cells were collected by centrifugation and counted with a haemocytometer. 50,000 cells were seeded per well in 96-well dishes and compounds were added according to the various treatment regimes to a final medium volume of 150 µl. For stimulation, phytohemagglutinin was added to a final concentration of 10 µg/ml. At day 3, proliferation was determined by AlamarBlue assay.

Measurement of Membrane Potential of Mitochondrial Membrane by TMRM Fluorescence Assay Murine 6.5 cells were treated for 20 min with the potentiometric fluorescent dye TMRM (tetramethylrhodamine methyl ester, AbD Serotec, 100 nM) and the fluorescence intensity was measured at 575 nm emission after excitation at 488 nm using a flow cytometer (CellLabQuanta, Beckman Coulter). This dye accumulates in the mitochondrial matrix when the inner membrane potential is more positive outside due to the extrusion of protons. For control, cells were pre-treated for 1 h with the uncoupling agent FCCP (carbonyl cyanide-p-trifluoromethoxyphenylhydrazone) which dissipates the membrane potential and abolishes fluorescence intensity. The effect of syrosingopine was assessed by pre-incubating cells with increasing concentrations of syrosingopine for 4 h as indicated, followed by TMRM staining.

The invention claimed is:

1. A pharmaceutical composition comprising syrosingopine and a mitochondrial inhibitor, wherein the mitochondrial inhibitor is metformin or phenformin.

2. The pharmaceutical composition of claim 1 wherein the mitochondrial inhibitor is metformin.

3. The pharmaceutical composition of claim 1 wherein the relative amount (weight per weight) of syrosingopine and the mitochondrial inhibitor is between 1 to 10 and 1 to 1'000.

4. The pharmaceutical composition of claim 2 wherein the relative amount (weight per weight) of syrosingopine and metformin is between 1 to 10 and 1 to 200.

* * * * *